United States Patent
Klesmith et al.

(10) Patent No.: US 11,155,811 B2
(45) Date of Patent: Oct. 26, 2021

(54) METHODS FOR GENERATING SINGLE- OR MULTI-SITE MUTAGENESIS

(71) Applicant: Board of Trustees of Michigan State University, East Lansing, MI (US)

(72) Inventors: Justin Klesmith, East Lansing, MI (US); James Stapleton, Eugene, OR (US); Timothy Whitehead, East Grand Rapids, MI (US); Emily Wrenbeck, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 16/115,029

(22) Filed: Aug. 28, 2018

(65) Prior Publication Data
US 2019/0062733 A1    Feb. 28, 2019

Related U.S. Application Data

(60) Provisional application No. 62/550,908, filed on Aug. 28, 2017.

(51) Int. Cl.
*C12N 15/10*    (2006.01)

(52) U.S. Cl.
CPC .......... *C12N 15/1082* (2013.01); *C12N 15/10* (2013.01); *C12N 15/102* (2013.01); *C12N 15/1058* (2013.01)

(58) Field of Classification Search
CPC .. C12N 15/1082; C12N 15/10; C12N 15/102; C12N 15/1058
See application file for complete search history.

(56) References Cited

U.S. PATENT DOCUMENTS

| | | | |
|---|---|---|---|
| 2013/0045507 A1* | 2/2013 | Huovinen | C12N 15/102 435/91.2 |
| 2013/0338043 A1* | 12/2013 | Firnberg | C07H 21/04 506/26 |

OTHER PUBLICATIONS

Gibson (Methods in Enzymology, vol. 498, 2011, pp. 349-361).*
Klesmith et al., "Comprehensive Sequence-Flux Mapping of a Levoglucosan Utilization Pathway in *E. coli*," ACS Syn Biol, 4(11):1235-1243 (2015).
Kowalsky et al., "Rapid Fine Conformational Epitope Mapping Using Comprehensive Mutaggenesis and Deep Sequencing," J Biol Chem, 290:26457-26470 (2015).
Kowalsky, "High Resolution Sequence-function Mapping of Full-Length Proteins," Michigan State University, 2015.
Whitehead et al., "Optimization of affinity, specificity and function of designed influenza inhibitors using deep sequencing," Nat Biotechnol, 30:543-548 (2012).

* cited by examiner

*Primary Examiner* — Robert H Havlin
(74) *Attorney, Agent, or Firm* — Foley Hoag LLP

(57) ABSTRACT

Deep mutational scanning is a foundational tool for addressing functional consequences of large numbers of mutants, yet a more efficient and accessible method for construction of user-defined mutagenesis libraries is needed. Provided herein are nicking saturation mutagenesis, a single-day, single-pot saturation mutagenesis method using routinely prepped plasmid dsDNA as input substrate. Reproducibility and convenience of the method are demonstrated through validation by an external research laboratory.

25 Claims, 5 Drawing Sheets
Specification includes a Sequence Listing.

A

B

A

B

METHODS FOR GENERATING SINGLE- OR MULTI-SITE MUTAGENESIS

RELATED APPLICATIONS

This application claims priority to U.S. Provisional Patent Application Ser. No. 62/550,908, filed on Aug. 28, 2017. This application is hereby incorporated herein by reference in its entirety.

STATEMENT OF RIGHTS

This invention was made with government support under CBET1254238 awarded by the National Science Foundation. The government has certain rights in the invention.

SEQUENCE LISTING

The instant application contains a Sequence Listing which has been filed electronically in ASCII format and is hereby incorporated by reference in its entirety. Said ASCII copy, created on Oct. 30, 2018, is named MSS-01501_SL.txt and is 3,662 bytes in size.

FIELD OF THE INVENTION

The present invention generally relates to the field of biotechnology and recombinant DNA technology and methods for generating single- or multi-site mutagenesis.

BACKGROUND

Mutational studies have been used for over six decades to probe protein sequence-function relationships. Deep mutational scanning has emerged as a method to assess the effect of thousands of mutations on function using massively parallel functional screens and DNA counting via deep sequencing (Fowler, D M et al. *Nat. Methods* 11, 801-807 (2014)). Information rich sequence-function maps obtained from such methods allow a researcher to address a variety of aims, including generation of biomolecular fitness landscapes (Firnberg, E et al. *Mol. Biol. Evol.* 31, 1581-1592 (2014); Stiffler, M A et al. *Cell* 160, 882-892 (2015); Hietpas, R T et al. *Proc. Natl. Acad. Sci.* 108, 7896-7901 (2011); Klesmith, J R et al. *ACS Synth. Biol.* 150922131145004 (2015)), therapeutic protein optimization (Whitehead, T A et al. *Nat. Biotechnol.* 30, 543-548 (2012)), and high-resolution conformational epitope mapping (Kowalsky, C A et al. *J. Biol. Chem.* 290, 26457-26470 (2015)). Although other technical challenges have been resolved (Kowalsky, C A et al. *PLoS One* 10, e0118193 (2015); Fowler, D M et al. *Nat. Protoc.* 9, 2267-2284 (2014)), a robust and accessible method for the construction of high quality, user-defined mutational libraries is lacking.

SUMMARY

Provided herein are plasmid-based mutagenesis methods for the preparation of comprehensive, single- or multi-site saturation DNA mutagenesis libraries. The methods include the successive creation and degradation of a wild-type template single-stranded DNA using nicking endonucleases followed by exonuclease degradation. Mutations are introduced by the annealing of a mutagenic oligonucleotide followed by strand extension using a thermostable DNA polymerase. New strands are closed using a thermostable ligase. Wildtype background DNA is degraded with treatment with DpnI.

Provided herein are methods comprising the steps of: (a) providing a double stranded nucleic acid molecule, wherein the nucleic acid molecule comprises a nickase recognition site; (b) providing a first nickase, wherein said first nickase nicks one strand of the nucleic acid molecule to create a first nicked strand and a remaining wild-type strand; (c) providing a first exonuclease, wherein said first exonuclease digests the first nicked strand; (d) providing at least one first mutagenic oligonucleotide, wherein said at least one first mutagenic oligonucleotide anneals to the remaining wild-type strand; (e) providing a first polymerase, wherein said first polymerase extends said at least one first mutagenic oligonucleotide around the remaining wild-type strand; (f) providing a first ligase, wherein said first ligase ligates the extended strand to form a double stranded nucleic acid comprising a mutant strand and a wild-type strand; (g) purifying the double stranded nucleic acid from step (f); (h) providing a second nickase, wherein said second nickase nicks the wild-type strand to create a second nicked strand and a remaining mutant strand; (i) providing a second exonuclease, wherein said second exonuclease digests the second nicked strand; (j) providing at least one second mutagenic oligonucleotide, wherein said at least one second mutagenic oligonucleotide anneals to the remaining mutant strand; (k) providing a second polymerase, wherein said second polymerase extends said at least one second mutagenic oligonucleotide around the remaining mutant strand; (l) providing a second ligase, wherein said second ligase ligates the extended strand to form a double stranded nucleic acid comprising a double stranded mutant nucleic acid molecule; and (m) purifying the double stranded mutant nucleic acid molecule from step (1). The nucleic acid molecule may be DNA, cDNA, or genomic DNA. In some embodiments, the nickase recognition site comprises a BbvCI restriction site. In some embodiments, the BbvCI restriction site is at least 7 base pairs. The nickase recognition site may be is Nt.BbvCI or Nb.BbvCI. In some embodiments, the exonuclease is Exonuclease I, Exonuclease III, or both. The polymerase may be Phusion Polymerase or Q5 DNA Polymerase. The ligase may be Taq DNA ligase. In some embodiments, at least one first or second mutagenic oligonucleotide is provided at a low primer:template ratio. The primer to template ratio may be 1:5, 1:10, 1:15, 1:20, 1:25, 1:30, 1:35, 1:40, 1:45, or 1:50. In some embodiments, the method further comprising the step of providing an enzyme to remove methylated nucleic acid molecules, hemimethylated nucleic acid molecules, or both. The mutation efficiency is enhanced to about 50%, about 55%, about 60%, about 65%, about 70%, about 75%, about 80%, about 85%, about 90%, about 92%, or about 94%, about 95%, about 96%, about 97%, about 98%, or about 99%. In some embodiments, the enhanced mutation efficiency is characterized with increased transformants or transformation output.

In some aspects, provided herein are methods of generating a double stranded mutant nucleic acid molecule. In some embodiments, the methods comprise the steps of (a) providing a double stranded wild-type nucleic acid molecule, wherein the nucleic acid molecule comprises a nickase recognition site; (b) nicking one strand of the nucleic acid molecule with a first nickase to create a first nicked strand and a remaining wild-type strand; (c) digesting said first nicked strand with a first exonuclease; (d) annealing at least one first mutagenic to the remaining wild-type strand;

(e) extending said at least one first mutagenic oligonucleotide around the remaining wild-type strand with a first polymerase; (f) ligating the extended strand with a first ligase to form a double stranded nucleic acid comprising a mutant strand and a wild-type; (g) purifying the double stranded nucleic acid from step (f); (h) nicking the wild-type strand with a second nickase to create a second nicked strand and a remaining mutant strand; (i) digesting said second nicked strand with a second exonuclease; (j) annealing at least one second mutagenic oligonucleotide to the remaining mutant strand; (k) extending said at least one second mutagenic oligonucleotide around the remaining mutant strand with a second polymerase; (l) ligating the extended strand with a second ligase to form a double stranded mutant nucleic acid molecule; and (m) purifying the double stranded mutant nucleic acid molecule from step (l). The nucleic acid molecule may be DNA, cDNA, or genomic DNA. The nickase recognition site may comprise a BbvCI restriction site. In some embodiments, the BbvCI restriction site is at least 7 base pairs. The nickase may be Nt.BbvCI or Nb.BbvCI. In some embodiments, the exonuclease is Exonuclease I, Exonuclease III, or both. The polymerase may be Phusion Polymerase or Q5 DNA Polymerase. The ligase may be Taq DNA ligase. In some embodiments, at least one first or second mutagenic oligonucleotide is provided at a low primer:template ratio. The primer to template ratio is 1:5, 1:10, 1:15, 1:20, 1:25, 1:30, 1:35, 1:40, 1:45, or 1:50. The methods provided herein may further comprise the step of providing an enzyme to remove methylated nucleic acid molecules, hemimethylated nucleic acid molecules, or both. In some embodiments, the mutation efficiency is enhanced to about 50%, about 55%, about 60%, about 65%, about 70%, about 75%, about 80%, about 85%, about 90%, about 92%, or about 94%, about 95%, about 96%, about 97%, about 98%, or about 99%.

In some embodiments, the enhanced mutation efficiency is characterized with increased transformants or transformation output. The methods provided herein may be used for generating single-site saturation mutagenesis, generating multi-site saturation mutagenesis. The mutagenesis may be a three single or one triple-mutation.

BRIEF DESCRIPTION OF THE DRAWINGS

The features, objects and advantages other than those set forth above will become more readily apparent when consideration is given to the detailed description below. Such detailed description makes reference to the following drawings, wherein.

Figure 1:
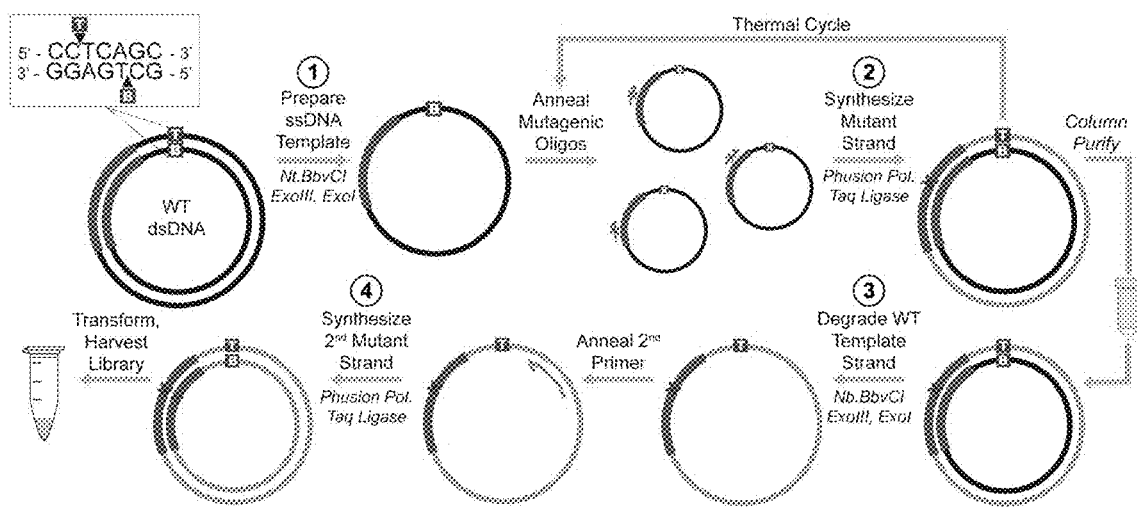
FIG. 1 shows a comprehensive single-site Nicking Saturation Mutagenesis (NSM). Plasmid dsDNA containing a 7-bp BbvCI recognition site is nicked by Nt.BbvCI. Exonuclease III degrades the nicked strand to generate an ssDNA template (step 1). Mutagenic oligos are then added at a 1:20 ratio with template, and Phusion Polymerase synthesizes mutant strands and Taq DNA Ligase seals nicks (step 2). The reaction is column purified, and then the wild-type template strand is nicked by Nb.BbvCI and digested by Exonuclease III digestion (step 3). A second primer is added and the complementary mutant strand is synthesized to yield mutagenized dsDNA (step 4).

While the invention is susceptible to various modifications and alternative forms, exemplary embodiments thereof are shown by way of example in the drawings and are described in detail below. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments herein and appended claims. Reference therefore should be made to the embodiments herein and appended claims for interpreting the scope of the invention.

DETAILED DESCRIPTION OF PREFERRED EMBODIMENTS

The compositions and methods now will be described more fully hereinafter with reference to the accompanying drawings, in which some, but not all embodiments are shown.

Although specific terms are employed herein, they are used in a generic and descriptive sense only and not for purposes of limitation. As such, unless defined otherwise, all technical and scientific terms used herein have the same meaning as commonly understood by one of skill in the art to which the invention pertains. Although any materials and methods similar to or equivalent to those described herein can be used in the practice or testing of the invention, the preferred methods and materials are described herein.

EXAMPLES

The invention will be more fully understood upon consideration of the following non-limiting examples, which are offered for purposes of illustration, not limitation.

Example 1: Materials and Methods

Reagents.

All chemicals were purchased from Sigma-Aldrich unless otherwise noted. All enzymes were purchased from New England Biolabs. All mutagenic oligos were designed using the QuikChange Primer Design Program (Agilent, Santa Clara, Calif.). Mutagenic oligos and sequencing primers were ordered from Integrated DNA Technologies (Coralville, Iowa).

Plasmid Construction.

All primer sequences used in this work are listed in Table 5. Plasmid pEDA5_GFPmut3_Y66H was prepared by modification of pJK_proB_GFPmut3 as described in Bienick et al. (Bienick, M S et al. *PLoS One* 9, (2014)) by a single Kunkel (Kunkel, T A et al. *Proc. Natl. Acad. Sci.* 82, 488-492 (1985)) reaction with two mutagenic primers: one encoding a BbvCI site (primer pED_BbvCI) and the second to introduce a Tyr66His point mutation (primer GFP_Y66H). pEDA3_amiE was constructed by altering pJK_proK17_amiE as described in Bienick et al. (Bienick, M S et al. *PLoS One* 9, (2014)) with a single Kunkel (Kunkel, T A et al. *Proc. Natl. Acad. Sci.* 82, 488-492 (1985)) reaction with two primers: one encoding a BbvCI site (pED_BbvCI) and the second encoding a mutated ribosome binding sequence (pED_kRBS3). pEDA5_GFPmut3_Y66H has been deposited in the AddGene repository (www.addgene.org).

Plasmid pSALECT-wtTEM1/csTEM1 was created as follows. Overhang PCR was used to add in an XhoI and BbvCI site after the existing NdeI site and before the original stop codon of plasmid pSALECT-EcoBam (Plasmid #59705, acquired from AddGene). A Δ2-23 truncation of wild-type TEM-1 β-lactamase was cloned in-frame between the NdeI and XhoI sites. A codon swapped Δ2-23 truncation of wild-type TEM-1 β-lactamase with a C-terminal His$_{6x}$ tag (SEQ ID NO: 1) and double stop codon was ordered as a gBlock (IDT) and was cloned in-frame between the XhoI and BbvCI site. This second TEM-1 β-lactamase is a C-terminal fusion to the wild-type TEM-1 beta-lactamase.

Comprehensive NSM Optimization.

The final optimized comprehensive NSM protocol is supplied in Example 3. 1× CutSmart Buffer (NEB) was used as an enzyme diluent when necessary. Two reactions were set up as follows: 0.76 pmol pEDA5_GFPmut3_Y66H was incubated with 10 U each of Nt.BbvCI and Exonuclease III in 1× CutSmart Buffer (20 μL final volume) for 60 minutes at 37° C. followed by enzyme inactivation at 80° C. for 20 minutes. 40 U of DpnI was added and the reaction was incubated at 37° C. for 60 minutes followed by 80° C. for 20 minutes. One reaction was then column purified by Zymo Clean & Concentrator (5:1 v/v ratio of binding buffer to sample), eluted in 6 μL Nuclease-Free H$_2$O (NFH$_2$O, Integrated DNA Technologies), transformed into XL1-Blue electrocompetent cells, and dilution plated. The following was added to the second reaction: 200 U of Taq DNA Ligase, 2 U Phusion High-Fidelity DNA Polymerase, 20 μL 5× Phusion HF Buffer, 20 μL 50 mM DTT, 1 μL 50 mM NAD$^+$, 2 μL 10 mM dNTPs, 29 μL NFH$_2$O (final reaction volume of 100 μL). The tube was placed into a preheated (98° C.) thermal cycler set with the following program: 98° C. for 2 minutes, 15 cycles of 98° C. for 30 seconds (denature), 55° C. for 45 seconds (anneal oligos), 72° C. for 7 minutes (extension), followed by a final incubation at 45° C. for 20 minutes to complete ligation. The reaction was column purified, transformed, and dilution plated as described above.

The optimization experiment including addition of Exonuclease I was performed as described below with the following modifications. A single mutagenic primer, His66Tyr (restores wild-type chromophore sequence), was used at a 1:20 primer:template ratio. The reaction was column purified and transformed into XL1 Blue electrocompetent cells as above. Green fluorescent (mutated) and white (parental) colonies were counted to calculate transformational and mutational efficiencies.

Comprehensive NSM of AmiE.

Two separate reactions targeting residues 100-170 and 171-241 of AmiE were performed. Mutagenic oligos programming degenerate codons (NNN) for each reaction were mixed in equimolar amounts to a final concentration of 10 μM. 20 μL of each primer mix was added to a phosphorylation reaction containing 2.4 μL of T4 Polynucleotide Kinase Buffer, 1 μL 10 mM ATP, 10 U T4 Polynucleotide Kinase, and incubated for 1 hour at 37° C. Secondary primer pED_2ND was phosphorylated in a reaction containing 18 μL NFH$_2$O, 2 μL T4 Polynucleotide Kinase Buffer, 7 μL 100 μM secondary primer, 1 μL 10 mM ATP, and 10 U T4 Polynucleotide Kinase. The reaction was incubated for 1 hour at 37° C. Phosphorylated NNN and secondary primers were diluted 1:1000 and 1:20 in NFH$_2$O, respectively.

ssDNA template was prepared in a reaction containing 0.76 pmol pEDA3_amiE dsDNA, 2 μL NEB CutSmart Buffer, 10 U Nt.BbvCI, 10 U Exonuclease III, 20 U Exonuclease I, and NFH$_2$O to 20 μL final reaction volume in a PCR tube. The following thermal cycle program was used: 37° C. for 60 minutes, 80° C. for 20 minutes (heat kill), hold at 4-10° C. Next, for mutant strand synthesis the following was added to each PCR tube on ice: 20 μL 5× Phusion HF Buffer, 20 μL 50 mM DTT, 1 μL 50 mM NAD$^+$, 2 μL 10 mM dNTPs, 4.3 μL 1:1000 diluted phosphorylated NNN mutagenic oligos, and 26.7 μL NFH$_2$O (final reaction volume of 100 μL). The tube contents were mixed, spun down, and placed on ice. 200 U of Taq DNA Ligase and 2 U Phusion High-Fidelity DNA Polymerase were added to each reaction, mixed, spun down, and placed into a preheated (98° C.) thermal cycler set with the following program: 98° C. for 2 minutes, 15 cycles of 98° C. for 30 seconds (denature), 55° C. for 45 seconds (anneal oligos), 72° C. for 7 minutes (extension), followed by a final incubation at 45° C. for 20 minutes to complete ligation. Additional 4.3 μL of oligos were added at the beginning of cycles 6 and 11. Each reaction was then column purified using a Zymo Clean & Concentrator kit (5:1 DNA Binding Buffer to sample). Each reaction was eluted in 15 μL NFH$_2$O, and 14 μL was transferred to a fresh PCR tube.

Next, for the template degradation reaction the following was added to each tube: 2 μL 10×NEB CutSmart Buffer, 1 U Nb.BbvCI, 2 U Exonuclease III, and 20 U Exonuclease I (20 μL final volume). The following thermocycler program was used: 37° C. for 60 minutes, 80° C. for 20 minutes (heat kill), hold at 4-10° C. To synthesize the second (complementary) mutant strand, the following was added to each reaction: 20 μL 5× Phusion HF Buffer, 20 μL 50 mM DTT, 1 μL 50 mM NAD$^+$, 2 μL 10 mM dNTPs, 3.3 μL 1:20 diluted phosphorylated secondary primer (0.38 pmol), and 27.7 µL NFH₂O (final reaction volume of 100 µQ. The tube contents were mixed, spun down, and placed on ice. 200 U of Taq DNA Ligase and 2 U Phusion High-Fidelity DNA Polymerase were added to each reaction, mixed, spun down, and placed into a preheated (98° C.) thermal cycler set with the following program: 98° C. for 30 seconds, 55° C. for 45 seconds, 72° C. for 10 minutes (can be extended for longer constructs), and 45° C. for 20 minutes.

To degrade methylated and hemimethylated wild-type DNA, 40 U of DpnI was added to each reaction and incubated at 37° C. for 1 hour. The final reaction was column purified using the Zymo Clean & Concentrator-5 kit as described above but eluted in 6 µL NFH₂O. The entire 6 µL was transformed into 40 µL of XL1-Blue electroporation competent cells (Agilent) and plated on Corning square bioassay dishes (Sigma-Aldrich, 245 mm×245 mm×25 mm). The following day, colonies were scraped with 15 mL of TB, vortexed, and 1 mL was removed and mini-prepped using a Qiagen Mini-prep Kit.

Single and Multi-Site NSM.

The final optimized single- and multi-site NSM protocol is supplied in Example 4. Mutagenic primers were phosphorylated separately following the protocol described above for the secondary primer, then diluted 1:20 with NFH₂O. For multi-site NSM, 2 µL of each primer was mixed in a single tube and diluted to a final volume of 40 µL. ssDNA template preparation was performed as described above. For mutant strand synthesis, oligos were annealed in the absence of polymerase as suggested by Firnberg et al. (Firnberg, E et al. *PLoS One* 7, e52031 (2012)). 3.3 µL of 1:20 phosphorylated oligos (single or mixed), 10 µL 5× Phusion HF Buffer, and 16.7 µL NFH₂O were added to the appropriate tube. Oligos were annealed with the following thermocycler program: 98° C. for 2 minutes, decrease to 55° C. over 15 minutes, 55° C. for 5 minutes, and hold at 55° C. While the reactions were held on the block, the following was added to each tube from a master mix: 20 µL 5× Phusion HF Buffer, 20 µL 50 mM DTT, 1 µL 50 mM NAD⁺, 2 µL 10 mM dNTPs, and 11 µL NFH₂O (final reaction volume of 100 µL). The tube contents were mixed by pipetting, then 200 U of Taq DNA Ligase and 2 U Phusion High-Fidelity DNA Polymerase were added to each reaction, mixed, spun down, and returned to the thermocycler for the following program: 72° C. for 10 minutes, 45° C. for 20 minutes. The remainder of the protocol proceeded as described in the comprehensive protocol.

DNA Deep Sequencing and Analysis.

Samples were prepared for deep sequencing as described in Kowalsky et al. (Kowalsky, C A et al. *PLoS One* 10, e0118193 (2015)) following Method B with the following adjustments: 15 cycles were used for both the first and second PCR, and no ExoI step was used. Sequences of PCR primers are listed in Table 5. The samples were pooled and sequenced on an Illumina MiSeq with 250 bp PE reads at the University of Illinois Chicago sequencing core. Read statistics are given in Table 1. Raw FASTQ files were analyzed with Enrich software (Fowler, D M et al. *Bioinformatics* 27, 3430-3431 (2011)) with modifications as described in Kowalsky et al. (Kowalsky, C A et al. *PLoS One* 10, e0118193 (2015)). Library statistics (Table 1) and read coverage plots (FIG. 3) were obtained using custom scripts freely available at Github (user JKlesmith). The full dataset is available at figshare (www.figshare.com).

Example 2

Random mutagenesis methods such as error-prone PCR suffer from limited codon sampling and imprecise control over the number of mutations introduced (Kitzman, J O et al. *Nat. Methods* 12, 203-206 (2015)). Of the published comprehensive saturation mutagenesis methods (Hietpas, R T et al. *Proc. Natl. Acad. Sci.* 108, 7896-7901 (2011); Kitzman, J O et al. *Nat. Methods* 12, 203-206 (2015); Firnberg, E et al. *PLoS One* 7, e52031 (2012); Jain, P C et al. *Anal. Biochem.* 449, 90-98 (2014); Fowler, D M et al. *Nat. Methods* 7, 741-746 (2010)), PFunkel (Firnberg, E et al. *PLoS One* 7, e52031 (2012)) offers the best combination of library coverage, mutational efficiency, control over number of mutations introduced, and scalability (Table 2). In particular, PFunkel can be used to prepare libraries covering all possible single point mutations, with most members of the library having exactly one mutation. However, PFunkel is limited by the required preparation of a uracil-containing ssDNA template by phage infection. dU-ssDNA yields are highly variable (Sambrook, J et al. *Molecular Cloning*. (Cold Spring Harbor Laboratory Press, 1989)) and the preparation adds at least two days to the mutagenesis procedure. By analogy to site-directed mutagenesis, PCR-based methods like QuikChange have mostly supplanted the highly efficient Kunkel mutagenesis that also requires dU-ssDNA (Kunkel, T A et al. *Proc. Natl. Acad. Sci.* 82, 488-492 (1985)).

TABLE 2

Performance metrics of published comprehensive mutagenesis methods

| Mutagenesis method Publication data gathered from Gene (# codons mutated) | Library type | Library coverage | Percent of mutants with NS mutations | | | Scalability mutatable codons/reaction |
|---|---|---|---|---|---|---|
| | | | Single | Zero | Multiple | |
| Casette Mutagenesis Hieptas et al. Hsp90 (9) | user-defined | 100% | nd | nd | nd | 20 |
| Error-Prone PCR Doolan et al. mouse PrP (211) | random | nd | 28.2% | 60.6% | 11.08% | all |
| Chemical Synthesis Fowler et al. hYAP65 WW domain (25) | random | 83.2% | nd | 20* | nd | 30 |

TABLE 2-continued

Performance metrics of published comprehensive mutagenesis methods

| Mutagenesis method Publication data gathered from Gene (# codons mutated) | Library type | Library coverage | Percent of mutants with NS mutations | | | Scalability mutatable codons/ reaction |
|---|---|---|---|---|---|---|
| | | | Single | Zero | Multiple | |
| PALS Mutagenesis Kitzman et al. Gal4 DBD and p53 (457 total) | user-defined | 94.3% | 35% | 29.2% | 33% | all |
| PFunkel Mutagenesis Kowalsky et al. Ct Cohesin (162) | user-defined | 97.1% | 73.6% | 20.5% | 5.9% | all |
| NSM This work AmiE (142 | user-defined | 100.0% | 64% | 26.8% | 9.3% | all |

(Hietpas, R T et al. *Proc. Natl. Acad. Sci.* 108, 7896-7901 (2011); Doolan, K M et al. *J. Mol. Biol.* 427, 328-340 (2015); Fowler, D M et al. *Nat. Methods* 7, 741-746 (2010); Kitzman, J O et al. *Nat. Methods* 12, 203-206 (2015); Firnberg, E et al. *PLoS One* 7, e52031 (2012)).
Bolded text indicates metrics that are comparatively inefficient to NSM and PFunkel mutagenesis.
NS = nonsynonymous.

Here, we present Nicking Saturation Mutagenesis (NSM), a new method that does not rely on dU-ssDNA. The protocol is shown schematically in FIG. 1 (full protocols are given in Examples 3-4). NSM is flexible, as any plasmid dsDNA can be used provided that it contains a single 7-bp BbvCI restriction site. The crux of NSM is the successive creation and degradation of a wild-type ssDNA template via a set of nicking endonucleases that recognize the same site, but nick one strand or the other, Nt.BbvCI and Nb.BbvCI, followed by exonuclease digestion. First, ssDNA template is created from dsDNA plasmid via a strand-specific nick introduced by Nt.BbvCI followed by selective digestion of the nicked strand with Exonuclease III (step 1; FIG. 1). Mutant strands are then synthesized by thermal cycling template DNA with mutagenic oligos at a low primer-to-template ratio to promote annealing of effectively one primer to each template (Firnberg, E et al. *PLoS One* 7, e52031 (2012)) (step 2). The highly processive and high fidelity Phusion Polymerase, chosen to minimize extension time, extends the primer around the circular template. Taq DNA Ligase closes the new strand to form a dsDNA plasmid with a mismatch at the mutational site. To avoid buffer incompatibility issues and prevent potential competition between Phusion and Exonuclease III, the heteroduplex DNA is then column purified.

To resolve the heteroduplex, the opposite strand nicking endonuclease, Nb.BbvCI, creates a nick in the template strand, which is subsequently degraded by Exonuclease III (step 3). A secondary primer is then added and synthesis of the complementary mutant strand follows as above (step 4). To reduce wild-type background, the final reaction is treated with DpnI to digest methylated and hemi-methylated parental DNA. The resulting protocol can be completed in a single day with minimal hands-on time (Table 3).

TABLE 3

Estimated time required for comprehensive library construction using NSM.

| Step number | | Hands-on time (min) | On-thermal cycler time (min) |
|---|---|---|---|
| 1* | Phosporylate oligos | 30 | 60* |
| 2* | ssDNA template strand preparation | 5 | 80* |

TABLE 3-continued

Estimated time required for comprehensive library construction using NSM.

| Step number | | Hands-on time (min) | On-thermal cycler time (min) |
|---|---|---|---|
| 3 | Comprehensive codon mutagenesis strand 1 | 10 | 146 |
| 4 | Column purification I | 5 | |
| 5 | Degrade template strand | 5 | 80 |
| 6 | Synthesize complimentary mutagenic strand | 10 | 32 |
| 7 | DpnI DNA cleanup | 2 | 60 |
| 8 | Column purification II | 5 | |
| | Subtotal (hr): | 1.2 | 6.6 |
| | Total (hr): | | 7.8 |

*Steps can be performed concurrently

*Steps can be performed concurrently

Figure 2:
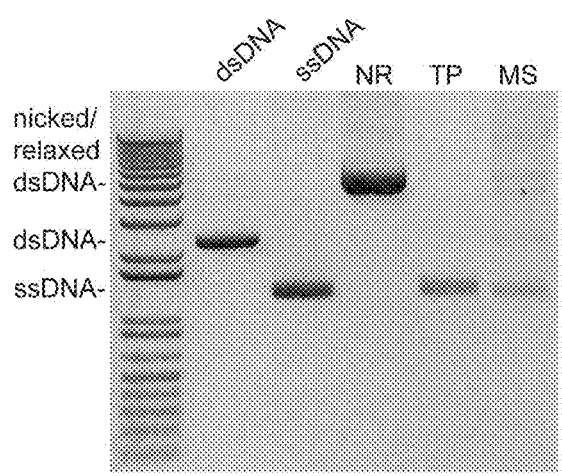
FIG. 2 depicts gel snapshots along the optimized NSM method. Plasmid dsDNA and ssDNA (prepared from bacteriophage) of pEDA5_GFPmut3 are included for size reference. NR=nicking reaction; 2 µg of pEDA5_GFPmut3_Y66H was placed in a 20 µL reaction with 10 U Nt.BbvCI in 1× CutSmart buffer. TP=template preparation; a reaction was ceased after the template preparation phase. MS=mutant strand; a reaction was ceased after the synthesis of the mutant strands, where regeneration of relaxed dsDNA can be seen.

We optimized NSM using a green/white fluorescent screen based on reversion of a non-fluorescent GFP mutant. A previously constructed GFPmut3 expression plasmid (Bienick, M S et al. *PLoS One* 9, (2014)) was modified by incorporating a BbvCI site and by changing the amino acid sequence of the GFPmut3 chromophore, Gly65-Tyr66-Gly67, to Gly65-His66-Gly67, resulting in a non-flurorescent protein. We performed NSM on this construct (pEDA5_GFPmut3_Y66H) with a restore-to-function mutagenic oligo (primer GFP_H66Y, see Table 4 for sequences). FIG. 2 shows gel snapshots at different stages along the optimized process.

TABLE 4

Primer sequences

Plasmid construction primers

| | | |
|---|---|---|
| pED_BbvCI | SEQ ID NO: 2 | gcggccccacgggtcctcagcgcgcatgat |
| pED_kRBS3 | SEQ ID NO: 3 | gacgagctaatatcgccatgtctcatatgtataaaaact tcttaaagttaaacaaaattatttctagaaag |
| GFP_Y66H | SEQ ID NO: 4 | gcaaagcattgaacaccatgaccgaaagtagtgacaagt |

Green/white screening mutagenic oligos

| | | |
|---|---|---|
| GFP_H66Y | SEQ ID NO: 5 | gcaaagcattgaacaccataaccgaaagtagtgacaagt |
| GFP_H66Y_RC | SEQ ID NO: 6 | acttgtcactactttcggttatggtgttcaatgctttgc |

Green/white screening secondary primer

| | | |
|---|---|---|
| pED_2ND | SEQ ID NO: 7 | ggtgattcattctgctaa |

Gene amplification: inner primers

| | | |
|---|---|---|
| amiE_NMT1_FWD | SEQ ID NO: 8 | gttcagagttctacagtccgacgatcgcaaatgtttggg gtgtg |
| amiE_T2_FWD | SEQ ID NO: 9 | gttcagagttctacagtccgacgatcctgcgatgacggt aat |
| amiE_T1_REV | SEQ ID NO: 10 | ccttggcacccgagaattccactctccaaatttccggat a |
| amiE_NMT2_REV | SEQ ID NO: 11 | ccttggcacccgagaattccattcgccgcattcacccag agt | blue = Illumina sequencing primer; black = gene overlap

Gene amplification: outer primers

| | | |
|---|---|---|
| Illumina_FWD | SEQ ID NO: 12 | aatgatacggcgaccaccgagatctacacgttcagagtt ctacagtccga |
| RPI30 | SEQ ID NO: 13 | caagcagaagacggcatacgagatCCGGTG gtgactggagttccttggcacccgagaattc |
| RPI31 | SEQ ID NO: 14 | caagcagaagacggcatacgagatATCGTG gtgactggagttccttggcacccgagaattcc | red = Illumina adapter sequence; BOLD = barcode; blue = Illumina sequencing primer Initial experiments with the full NSM protocol showed a mutational efficiency of 23% with 3×10$^5$ transformants. To determine the sources of high wild-type background, we performed a series of control experiments containing no mutagenic primer. Thus, any resulting transformants could be unambiguously attributed to wild-type. The number of background transformants was 10$^3$ after the template preparation step and incubation with DpnI, but increased to 10$^6$ if the reaction was allowed to proceed through the thermocycling steps. We hypothesized that short stretches of incompletely degraded DNA were priming and regenerating wild-type constructs. To remedy this, Exonuclease I, which specifically degrades ssDNA, was added to both the template preparation and degradation reactions. The addition of Exonuclease I improved mutational efficiency to 56% with >5×10$^5$ transformants. Incubation of the final reaction mixture with DpnI to remove methylated and hemimethylated wild-type DNA increased the mutational efficiency to 68% with >3×10$^5$ transformants.

The orientation of the BbvCI site determines the directionality of designed mutagenic oligos (see Example 5). To confirm that the order of nicking enzymes could be switched, we performed NSM using green/white screening in two reactions: one with Nt.BbvCI then Nb.BbvCI using the GFP_H66Y mutagenic primer (priming one strand), and the second using Nb.BbvCI first with the GFP_H66Y_RC primer (priming the opposite strand at the same location as GFP_H66Y). We observed mutational efficiencies of 46% and 44% with >8×10$^4$ and >9×10$^4$ total transformants, respectively, confirming that the order of nicking enzymes can be switched.

Figure 3:
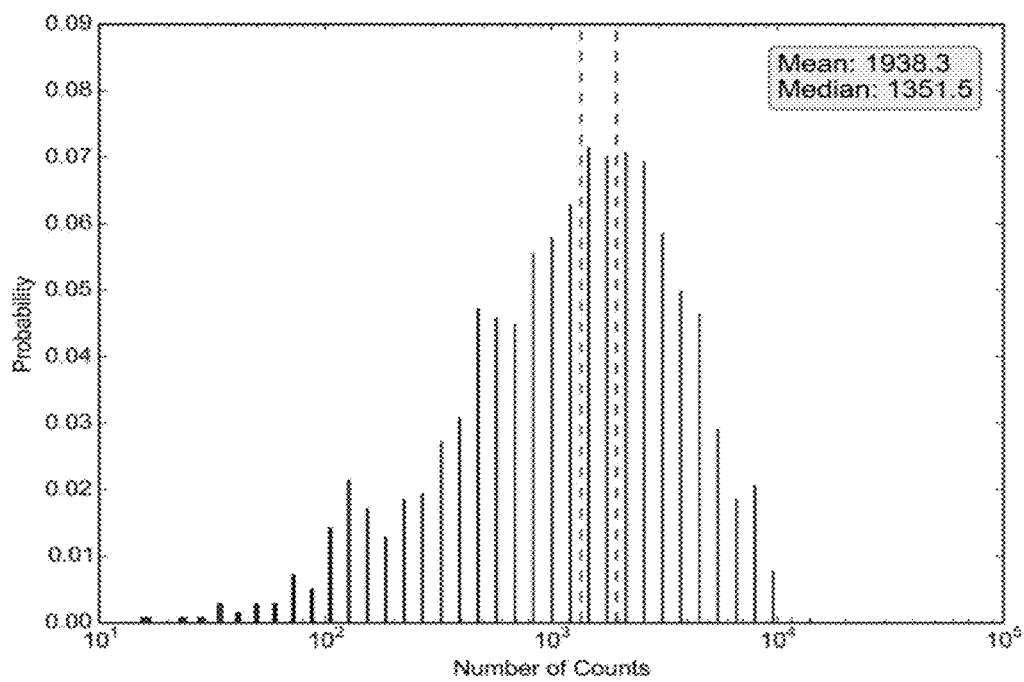
FIG. 3 contains 2 panels, labeled as A and B, depicting probability distribution of mutation counts in unselected AmiE comprehensive NSM libraries. Dashed vertical lines represent median (red) and mean (blue) library member read coverage. Panel A shows distribution for Tile 1 and panel B shows the distribution for Tile 2.
Figure 3:
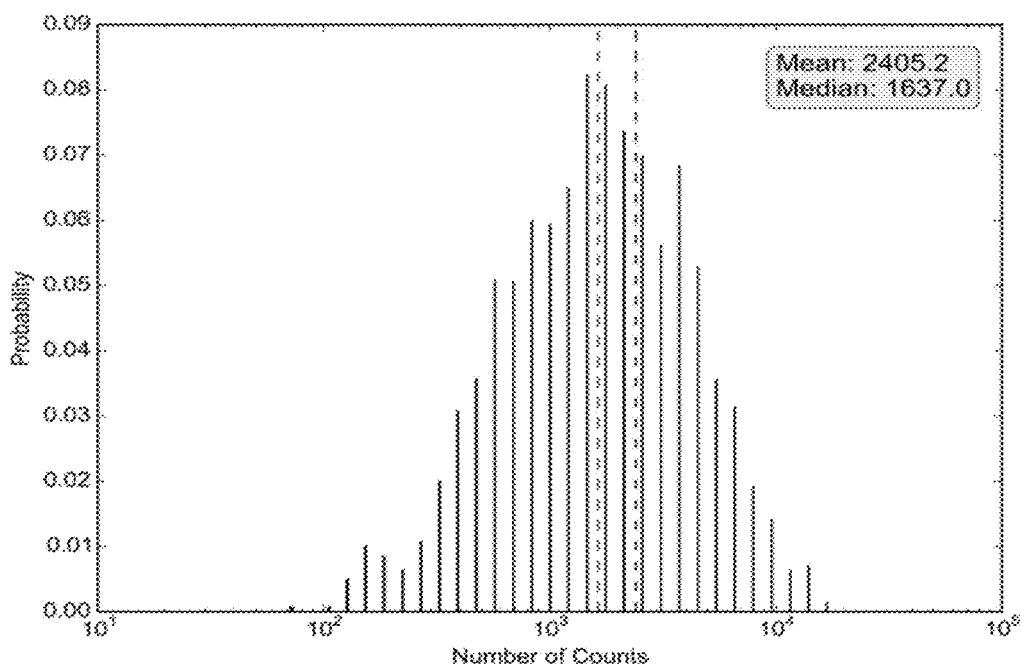
Figure 4:
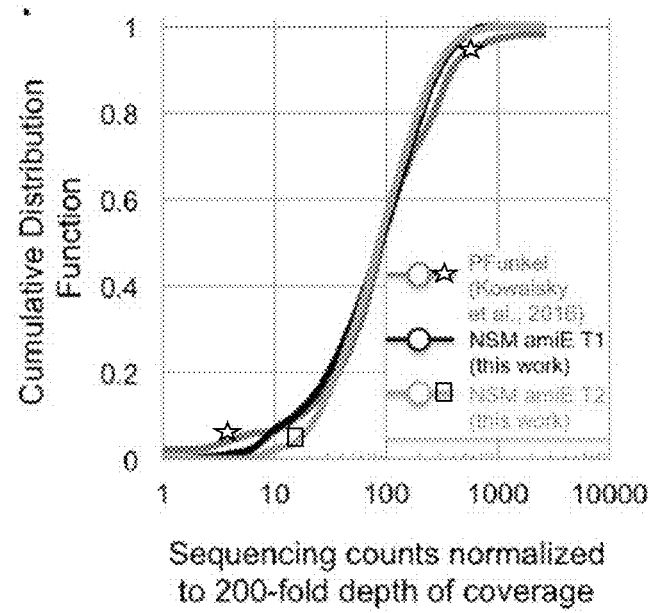
FIG. 4 contains 2 panels, labeled as A and B, showing a comparison of the probability distributions of site-saturation mutagenesis libraries resulting from NSM or PFunkel mutagenesis (Firnberg, E et al. *PLoS One* 7, e52031 (2012); Kowalsky. In preparation). Because the depth of sequencing coverage varied between the three methods, all samples were normalized to a 200-fold depth of coverage of possible single non-synonymous mutations. The expected library diversity is 820 for Kowalsky et al. (Kowalsky. In preparation) and 1420 for AmiE T1 & T2 (this work). Panel A shows cumulative distribution function for the three libraries as a function of normalized sequencing counts. 91.7%, 93.2%, and 97.8% of the library is represented above a threshold of 10 sequencing counts for PFunkel library, AmiE T1, and the AmiE T2 libraries, respectively. Panel B shows frequency plotted as a function of sequencing counts for the same three libraries. The experimental data are plotted as symbols, with lines representing a best fit of the data using a log-normal distribution (PFunkel: $\mu=2$, $\sigma=0.49$, AmiE T1: $\mu=2$, $\sigma=0.50$. AmiE T2: $\mu=2$, a=0.44).
Figure 4:
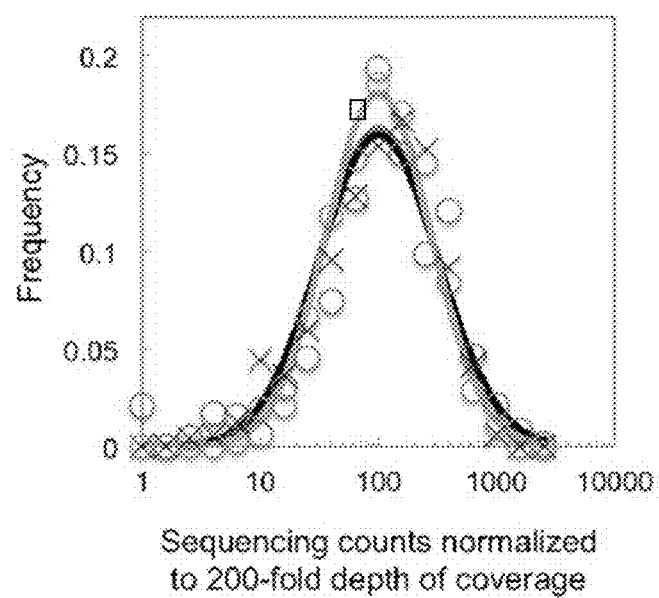

Next, we used NSM to prepare comprehensive single-site saturation mutagenesis libraries for two different 71 codon stretches of an aliphatic amidase (Tile 1 and 2 correspond to residues 100-170, and 171-241, respectively) (Bienick, M S et al. *PLoS One* 9, (2014)). A mixture of 71 degenerate NNN oligos sets, each with three consecutive randomized bases (NNN) corresponding to one of the 71 codons, was used at a 1:20 primer:template ratio. We deep sequenced the resulting libraries to an average depth of coverage of 2,200 reads per variant and processed the data using Enrich (Fowler, D M et al. *Bioinformatics* 27, 3430-3431 (2011)). We observed 100% of possible single non-synonymous (NS) mutants (2840 total) and 100% of all possible programmed codon mutations (8946 total) (library coverage statistics are shown in Table 1). 64.4% and 63.5% of library members had exactly one NS mutation for AmiE Tile 1 and AmiE Tile 2, respectively. The frequency of individual mutations in each library followed a log-normal distribution, which is consistent with libraries prepared by PFunkel mutagenesis (Klesmith, J R et al. ACS Synth. Biol. 150922131145004 (2015); Kowalsky, C A et al. PLoS One 10, e0118193 (2015)) (FIG. 3). In deep mutational scanning experiments the initial library is typically sequenced at approximately 200-fold depth of coverage of the expected diversity. Normalizing the above sequencing results to a 200-fold depth of coverage reveal that 93.2% and 97.8% of possible NS mutations would be represented above the typical threshold of 10 sequencing reads for AmiE Tile 1 and Tile 2, respectively (FIG. 4A). This compares favorably with PFunkel mutagenesis (91.7% using the same threshold), although we note that the library distributions between the two methods are essentially identical (FIG. 4B).

TABLE 1

NSM library coverage statistics.

|  | Tile 1 (residues 100-170) | Tile 2 (residues 171-241) |
|---|---|---|
| Sequencing reads passing through Enrich [17] | 4273346 | 5378051 |
| Percent of possible codon substitutions observed |  |  |
| 1-bp substitution | 100.0 | 100.0 |
| 2-bp substitution | 100.0 | 100.0 |
| 3-bp substitution | 100.0 | 100.0 |
| All substitutions | 100.0 | 100.0 |
| Percent of reads with: |  |  |
| No nonsynonymous mutations | 27.2 | 26.3 |
| One nonsynonmymous mutation | 64.4 | 63.5 |
| Multiple nonsynonymous mutations | 8.4 | 10.2 |
| Coverage of possible single amino acid substitutions with ≥ 10 reads (1420 total) | 100.0 | 100.0 |
| Coverage of possible programmed mutant codons with ≥ 10 reads (4473 total) | 100.0 | 100.0 |

Figure 5:
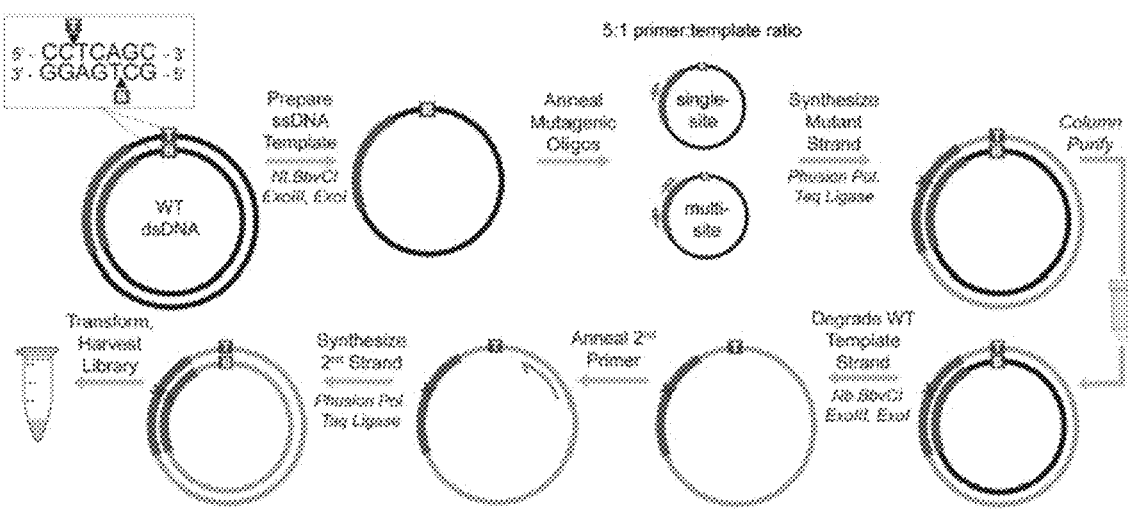
FIG. 5 depicts a schematic overview of single- or multi-site NSM. After the preparation of an ssDNA template, an annealing reaction is set up with a single or mixed set of mutagenic oligos at a 5:1 primer:template ratio (for each oligo). Next, reagents and enzymes necessary to synthesize the mutant strands are added. The remainder of the protocol is identical to comprehensive NSM.

To further expand the utility of NSM, we developed a single- and multi-site protocol (FIG. 5 and Example 4). The protocol was modified by adding primer at a 5:1 molar ratio to template and altering the thermal cycling steps for mutant strand synthesis (see Methods). We tested the method by performing three single- and one triple-mutation NSM reaction to TEM-1 β-lactamase (plasmid pSALECT-wtTEM1/csTEM1). Sanger sequencing of two clones from each of the three single-site reactions revealed that ⅚ clones contained a single mutation. For the multi-site reaction, 5 out of 10 sequenced clones contained the desired three programmed mutations.

Robust and effective molecular biology methods are characterized by the ease of their adoption by laboratories outside of where they were developed. To evaluate the accessibility of NSM, an external lab tested the method by performing single-site NSM on the pEDA5_GFPmut3_Y66H plasmid with the restore-to-function oligo GFP_H66Y. The resulting mutational efficiency, calculated by counting fluorescent (mutant) and non-fluorescent (wild-type) colonies, was 86.8±6.1% (n=3 independent experiments).

The cost of NSM could be further decreased by replacing the individually synthesized oligos used in this study with micro-array derived oligos (Kosuri, S et al. Nat. Methods 11, 499-507 (2014)) (Table 5). Because in NSM the template is in excess to the mutational primer, we hypothesized that oligo dsDNA PCR-amplified from micro-arrays can be used directly without purification to single-stranded form. To test this, we performed NSM using green/white screening in the presence of both the GFP_H66Y primer and its reverse complement, GFP_H66Y_RC. The desired mutation was detected at a rate of 52% with >3×10$^6$ total transformants. This proof-of-concept demonstrates that dsDNA oligos can be used for NSM.

TABLE 5

Cost analysis of NSM compared with PFunkel mutagenesis (Fimberg, E et al. PLoS One 7, e52031 (2012)).

|  | PFunkel | NSM | NSM + oligo pools |
|---|---|---|---|
| Library preparation cost per reaction | $53 | $55 | $55 |
| NNN oligo cost per codon (source) | $4 (IDT) | $4 (IDT) | $0.39 (CustomArray) |
| Total cost per 100 scanned codons | $453 | $455 | $94 |

Library preparation cost was calculated by totaling cost of enzymes (price information gathered from New England Biolabs) and reagents (price information gathered from Sigma-Aldrich, Qiagen, and Zymo Research) on a per reaction basis.
Microarray derived oligo cost was calculated based on ≤ 79 bp oligo pools from CustomArray ($1600/12,472 features).
Cost of an NNN degenerate oligo synthesized in triplicate is $1600 * (3/12,472) = $0.39.
Price of chemically synthesized degenerate NNN oligos based on IDT pricing for a 40 bp primer[8] at the 500 pmole scale: $0.10/base * 40 bp = $4/codon.
Prices obtained February 2016.

We have demonstrated a single-pot, single-day, inexpensive method for the preparation of comprehensive single- and multi-site saturation mutagenesis libraries from plasmid dsDNA. Although in the presented work comprehensive single-site saturation libraries were prepared, the utility of NSM is not limited to saturation mutagenesis. Because codon substitutions are user defined, the end user may restrict diversity to specific residues such as hydrophobic or charged substitutions.

To validate the performance of NSM we used "testers" from an external lab; we propose using such testers to enhance reproducibility and accessibility of new molecular biology methods (Nat Biotech 30, 806 (2012)). To aid in method adoption, the GFP plasmid used for green/white screening has been deposited to the AddGene repository (www.addgene.org) as a tool for practicing and troubleshooting the method.

Example 3: Comprehensive Site-Saturation NSM Protocol

Plasmid dsDNA should be prepared fresh (<1 month old, avoid freeze/thaw) from a dam+E. coli strain (i.e. XL1-Blue), and should be at a concentration sufficient to add 0.76 pmol dsDNA in ≤15 µL. Quality of the input dsDNA substrate is important. Mutagenic oligos are designed using the Agilent QuikChange Primer Design Program (www.agilent.com). Troubleshooting: Green/white fluorescent screening can be used to troubleshoot or learn the method. Plasmid pEDA5_GFPmut3_Y66H contains a constitutively expressed non-fluorescent GFPmut3 variant with a mutated chromophore (Gly65-Tyr66-Gly67 to Gly65-His66-Gly67). A single mutagenic oligo, GFP_H66Y, encodes the restore-to-function mutation resulting in fluorescent 'mutants'. The protocol can be followed as below with the following adjustments:

1. 20 μL of 10 μM GFP_H66Y primer is added to the phosphorylation reaction (single primer as opposed to a primer mix).
2. The secondary primer used is pED_2ND (primer sequences listed at end of protocol).
3. Prepare serial dilution plates of the transformation to calculate transformation and mutational efficiencies.

Materials:
Zymo Clean & Concentrator-5 kit (Zymo Research)
Corning square bioassay dishes, 245 mm×245 mm×25 mm (Sigma-Aldrich)
High-efficiency electrocompetent cells (e.g. Agilent XL1-Blue Electroporation Competent cells, #200228)

Reagents:
Nuclease-Free H$_2$O (NFH$_2$O, Integrated DNA Technologies)
Plasmid dsDNA (see notes above on preparation)
Mutagenic and secondary primers
T4 Polynucleotide Kinase Buffer (NEB)
10 mM ATP
10× CutSmart Buffer (NEB)
5× Phusion HF Buffer (NEB)
10 mM ATP
50 mM DTT
50 mM NAD$^+$
10 mM dNTPs Enzymes* (all purchased from NEB):
T4 Polynucleotide Kinase (10 U/μL)
Nt.BbvCI (10 U/μL)
Nb.BbvCI (10 U/μL)
Exonuclease III (100 U/μL)
Exonuclease I (20 U/μL)
Phusion High-Fidelity DNA Polymerase (2 U/μL)
Taq DNA Ligase (40 U/μL)
DpnI (20 U/μL)
*Diluent for all enzymes is 1×NEB CutSmart Buffer Protocol
1.) Phosphorylate Oligos
1. Make a mixture of NNN/NNK mutagenic oligos at final concentration of 10 μM.
2. Into a PCR tube, add:

| | |
|---|---|
| 20 μL | 10 μM mutagenic oligo mixture |
| 2.4 μL | T4 Polynucleotide Kinase Buffer |
| 1 μL | 10 mM ATP |
| 1 μL | T4 Polynucleotide Kinase (10 U/μL) |

3. In a separate PCR tube add:

| | |
|---|---|
| 18 μL | NFH$_2$O |
| 3 μL | T4 Polynucleotide Kinase Buffer |
| 7 μL | 100 μM secondary primer |
| 1 μL | 10 mM ATP |
| 1 μL | T4 Polynucleotide Kinase (10 U/μL) |

4. Incubate at 37° C. for 1 hour.
5. Store phosphorylated oligos at −20° C. The day of mutagenesis, dilute phosphorylated mutagenic oligos 1:1000 and secondary primer 1:20 in NFH$_2$O.

2.) ssDNA Template Strand Preparation
Add the following into PCR tube(s):

| | |
|---|---|
| 0.76 pmol | Plasmid dsDNA |
| 2 μL | 10X CutSmart Buffer |

-continued

| | |
|---|---|
| 1 μL | 1:10 diluted Exonuclease III (final concentration of 10 U/μL) |
| 1 μL | Nt.BbvCI (10 U/μL) |
| 1 μL | Exonuclease I (20 U/μL) |
| NFH$_2$O to 20 μL | final volume |

PCR Program:

| | |
|---|---|
| 37° C. | 60 minutes |
| 80° C. | 20 minutes |
| 4-10° C. | Hold |

3.) Comprehensive Codon Mutagenesis Strand 1
Add the following into each tube (100 μL final volume):

| | |
|---|---|
| 26.7 μL | NFH$_2$O |
| 20 μL | 5X Phusion HF Buffer |
| 4.3 μL | 1:1000 diluted phosphorylated mutagenic oligos |
| 20 μL | 50 mM DTT |
| 1 μL | 50 mM NAD$^+$ |
| 2 μL | 10 mM dNTPs |
| 1 μL | Phusion High Fidelity Polymerase (2 U/μL) |
| 5 μL | Taq DNA Ligase (40 U/μL) |

PCR Program:
98° C. 2 minutes
98° C. 30 seconds
55° C. 45 seconds→×15 cycles; add additional 4.3 μL oligo
72° C. 7 minutes at beginning of cycles 6 and 11
45° C. 20 minutes
4-10° C. Hold 4.) Column Purification Using a Zymo Clean and Concentrate Kit
Following the manufacturer's instructions:
  1. Add 5 volumes of DNA binding buffer to each reaction and mix
  2. Transfer to a Zymo-Spin Column in a collection tube
  3. Centrifuge at maximum speed for 30 seconds and discard flow through
  4. Add 200 μL of DNA wash buffer to the column
  5. Centrifuge at maximum speed for 30 seconds and discard flow through
  6. Repeat steps 4 and 5
  7. Add 15 μL of NFH$_2$O directly to the column in a new clean 1.5 mL microfuge tube and incubate at room temperature for 5 minutes
  8. Centrifuge at maximum speed for one minute 5.) Degrade Template Strand
Transfer 14 μL of the purified DNA product to a PCR tube, then add (20 μL final volume):

| | |
|---|---|
| 2 μL | 10X CutSmart Buffer |
| 2 μL | 1:50 diluted Exonuclease III (final concentration of 2 U/μL) |
| 1 μL | 1:10 Nb.BbvCI (final concentration of 1 U/μL) |
| 1 μL | Exonuclease I (20 U/μL) |

PCR Program:

| 37° C. | 60 minutes |
|---|---|
| 80° C. | 20 minutes |
| 4-10° C. | Hold |

6.) Synthesize 2$^{rd}$ (Complementary) Mutagenic Strand

To above PCR tube, add (100 μL final volume):

| 27.7 μL | NFH$_2$O |
|---|---|
| 20 μL | 5X Phusion HF Buffer |
| 3.3 μL | 1:20 diluted phosphorylated secondary primer |
| 20 μL | 50 mM DTT |
| 1 μL | 50 mM NAD$^+$ |
| 2 μL | 10 mM dNTPs |
| 1 μL | Phusion High Fidelity Polymerase (2 U/μL) |
| 5 μL | Taq DNA Ligase (40 U/μL) |

PCR Program:

| 98° C. | 30 seconds |
|---|---|
| 55° C. | 45 seconds |
| 72° C. | 10 minutes |
| 45° C. | 20 minutes |
| 4-10° C. | Hold |

7.) DNA cleanup

Add into each reaction:

| 2 μL | DpnI (20 U/μL) |
|---|---|

PCR Program:

| 37° C. | 60 minutes |
|---|---|

8.) Zymo Clean and Concentrate Kit

Follow instructions in step 4 but elute in 6 μl, of NFH$_2$O.

9.) DNA Transformation

Transform the entire 6 μL reaction product into a high-efficiency cloning strain following standard transformation protocols. After recovery, bring the final volume of the transformation to 2-2.5 mL with additional sterile media. Spread on to a prepared large BioAssay dish (245 mm×245 mm×25 mm, Sigma-Aldrich). Additionally, serial dilution plates should be prepared to calculate transformation efficiencies. Incubate overnight at 37° C. The next day, scrape the plate using 5-10 mL of LB or TB. Vortex the cell suspension and extract the library plasmid dsDNA using a mini-prep kit (Qiagen) of a 1 mL aliquot of the cell suspension. Additional mini-preps (or a midi-prep) can be done if large amounts of library DNA are required.

GFP_H66Y:  gcaaagcattgaacaccataaccgaaagtagtgacaagt pED_2ND:   ggtgattcattctgctaa Example 4: Single- or Multi-Site NSM Protocol See Notes, Troubleshooting, Materials, Reagents, and Enzymes sections from Example 3

Protocol:

1.) Phosphorylate Oligos

Phosphorylate each oligo separately and then mix to obtain a final dilute oligo mixture.

1. To phosphorylate each NNN/NNK oligo, in PCR tubes add:

| 18 μL | NFH$_2$O |
|---|---|
| 3 μL | T4 Polynucleotide Kinase Buffer |
| 7 μL | 100 μM mutagenic oligo |
| 1 μL | 10 mM ATP |
| 1 μL | T4 Polynucleotide Kinase (10 U/μL) |

2. To phosphorylate the secondary primer, in a separate PCR tube add:

| 18 μL | NFH$_2$O |
|---|---|
| 3 μL | T4 Polynucleotide Kinase Buffer |
| 7 μL | 100 μM secondary primer |
| 1 μL | 10 mM ATP |
| 1 μL | T4 Polynucleotide Kinase (10 U/μL) |

3. Incubate at 37° C. for 1 hour.
4. Dilute phosphorylated oligos 1:20. If performing multi-site NSM, add 2 μL of each oligo into a single tube, then add NFH$_2$O to 40 μL final volume. Dilute secondary primer 1:20.

2.) ssDNA Template Strand Preparation

Add the following into PCR tube(s):

| 0.76 pmol | Plasmid dsDNA |
|---|---|
| 2 μL | 10X CutSmart Buffer |
| 1 μL | 1:10 diluted Exonuclease III (final concentration of 10 U/μL) |
| 1 μL | Nt.BbvCI (10 U/μL) |
| 1 μL | Exonuclease I (20 U/μL) |
| NFH$_2$O to 20 μL | final volume |

PCR Program:

| 37° C. | 60 minutes |
|---|---|
| 80° C. | 20 minutes |
| 4-10° C. | Hold |

3.) Anneal Oligos

Add the following to the appropriate tube (50 μL final volume):

| 16.7 μL | NFH$_2$O |
|---|---|
| 3.3 μL | 1:20 diluted mutagenic oligos (single or mixed) |
| 10 μL | 5X Phusion HF Buffer |

PCR Program:

| 98° C. | 2 minutes |
|---|---|
| gradually decrease to 55° C. over 15 minutes | |

4.) Single- or Multi-Site Mutagenesis Strand 1
Keeping the tubes on the thermocyler, add the following into each tube (1004 final volume):

| | |
|---|---|
| 11 µL | NFH₂O |
| 10 µL | 5X Phusion HF Buffer |
| 20 µL | 50 mM DTT |
| 1 µL | 50 mM NAD⁺ |
| 2 µL | 10 mM dNTPs |
| 5 µL | Taq DNA Ligase (40 U/µL) |
| 1 µL | Phusion HF Polymerase (2 U/µL) |

PCR Program:

| | |
|---|---|
| 72° C. | 10 minutes |
| 45° C. | 20 minutes |
| 4-10° C. | Hold |

5.) Column Purification Using a Zymo Clean and Concentrate Kit
Following the manufacturer's instructions:
1. Add 5 volumes of DNA binding buffer to each reaction and mix
2. Transfer to a Zymo-Spin Column in a collection tube
3. Centrifuge at maximum speed for 30 seconds and discard flow through
4. Add 200 µL of DNA wash buffer to the column
5. Centrifuge at maximum speed for 30 seconds and discard flow through
6. Repeat steps 4 and 5
7. Add 15 µL of NFH₂O directly to the column in a new clean 1.5 mL microfuge tube and incubate at room temperature for 5 minutes
8. Centrifuge at maximum speed for one minute 6.) Degrade Template Strand
Transfer 14 µL of the purified DNA product to a PCR tube, then add (20 µL final volume):

| | |
|---|---|
| 2 µL | 10X CutSmart Buffer |
| 2 µL | 1:50 diluted Exonuclease III (final concentration of 2 U/µL) |
| 1 µL | 1:10 diluted Nb.BbvCI (final concentration of 1 U/µL) |
| 1 µL | Exonuclease I (20 U/µL) |

PCR Program:

| | |
|---|---|
| 37° C. | 60 minutes |
| 80° C. | 20 minutes |
| 4-10° C. | Hold |

7.) Synthesize 2$^{nd}$ (Complementary) Mutagenic Strand
To each tube, add (100 µL final volume):

| | |
|---|---|
| 27.7 µL | NFH₂O |
| 20 µL | Phusion HF Buffer |
| 3.3 µL | 1:20 diluted phosphorylated secondary primer |
| 20 µL | 50 mM DTT |
| 1 µL | 50 mM NAD⁺ |
| 55° C. | 5 minutes |
| 55° C. | Hold |
| 2 µL | 10 mM dNTPs |
| 1 µL | Phusion High Fidelity Polymerase (2 U/µL) |
| 5 µL | Taq DNA Ligase (40 U/µL) |

PCR Program:

| | |
|---|---|
| 98° C. | 30 seconds |
| 55° C. | 45 seconds |
| 72° C. | 10 minutes |
| 45° C. | 20 minutes |
| 4-10° C. | Hold |

8.) DNA cleanup
Add into each reaction:

| | |
|---|---|
| 2 µL | DpnI (20 U/µL) |

PCR Program:

| | |
|---|---|
| 37° C. | 60 minutes |

9.) Zymo Clean and Concentrate Kit
Follow instructions in step 5 but elute in 6 µL NFH₂O.
10.) DNA Transformations
Transform entire 6 µL reaction product as described in Example 3.

Example 5: Orientation of BbvCI Site and Design of Primers

In oligonucleotide-programmed mutagenesis, mutagenic oligos are designed to be complementary to the wild-type template sequence on either side of the programmed mutation such that they can anneal to the template. For Kunkel mutagenesis (Kunkel, T A *Proc. Natl. Acad. Sci.* 82, 488-492 (1985)), the ssDNA template strand is made by replication and packaging within a phage host. The directionality of the ssDNA template strand (sense or anti-sense) is dependent upon the directionality of the F1-origin of replication. If the F1-origin is such that the template strand made is sense, then mutagenic oligos are designed anti-sense.

For NSM, the directionality of the template strand is dependent upon the orientation of the BbvCI site. The set of enzymes, Nt.BbvCI (Nick-top BbvCI) and Nb.BbvCI (Nick-bottom BbvCI) will create nicks on the strands containing their respective recognition sequence. If the Nt.BbvCI nicking enzyme is used for template preparation and its recognition sequence is encoded on the anti-sense strand, the ssDNA template formed will be sense. Thus, mutagenic oligos should be designed anti-sense. The opposite is true if Nb.BbvCI was used to create the template strand.

Example 6: Testing Q5 DNA Polymerase in Comprehensive Nicking Mutagenesis

To test the use of Q5 DNA Polymerase (New England Biolabs) as a substitute for Phusion Polymerase, comprehensive nicking mutagenesis reactions using pEDA5_GFP_H66Y positive control plasmid were performed using 1 µL Q5 in either Phusion HF Buffer or Q5 Buffer, along with a positive control (1 µL Phusion Polymerase in Phusion Buffer). Reactions were transformed into house-made XL1-Blue electrocompetent cells, dilution plated, and the following day mutant (green) colonies along with total colonies were counted. We found that Q5 Polymerase in Phusion Buffer outperformed Phusion, resulting in 93.8% mutational efficiency (mutant colonies/total colonies) and >2.75-fold total transformants (Table 6). However, Q5 Polymerase in combination with Q5 Buffer yielded 5.6% transformational efficiency and less than half of the total transformants. As Taq DNA Ligase is affected by buffer choice, we hypothesize that Phusion HF Buffer is favorable to Q5 Buffer for Taq Ligase activity. These results indicate that Q5 Polymerase can substitute for Phusion, however further optimization of buffer conditions is needed to remove the requirement of Phusion Buffer. Of note, this data represents a single experiment.

TABLE 6

Testing Q5 DNA Polymerase in comprehensive nicking mutagenesis.

| Polymerase | Buffer | Mutant colonies | Total colonies | Mutational efficiency |
| --- | --- | --- | --- | --- |
| 1 uL Phusion | Phusion | 3800 | 5800 | 65.5% |
| 1 uL Q5 | Phusion | 15000 | 16000 | 93.8% |
| 1 uL Q5 | Q5 | 100 | 1800 | 5.6% |

INCORPORATION BY REFERENCE

The contents of all references, patent applications, patents, and published patent applications, as well as the Figures and the Sequence Listing, cited throughout this application are hereby incorporated by reference.

EQUIVALENTS

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

What is claimed is:

1. A method comprising the steps of:
   (a) providing a double stranded nucleic acid molecule, wherein the double stranded nucleic acid molecule comprises a BbvCI nickase recognition site;
   (b) providing a first nickase, wherein said first nickase nicks one strand of the nucleic acid molecule to create a first nicked strand and a remaining wild-type strand;
   (c) providing a first exonuclease, wherein said first exonuclease digests the first nicked strand;
   (d) providing at least one first mutagenic oligonucleotide, wherein said at least one first mutagenic oligonucleotide anneals to the remaining wild-type strand;
   (e) providing a first polymerase, wherein said first polymerase extends said at least one first mutagenic oligonucleotide around the remaining wild-type strand;
   (f) providing a first ligase, wherein said first ligase ligates the extended strand to form a double stranded nucleic acid comprising a mutant strand and a wild-type strand;
   (g) purifying the double stranded nucleic acid from step (f);
   (h) providing a second nickase, wherein said second nickase nicks the wild-type strand to create a second nicked strand and a remaining mutant strand;
   (i) providing a second exonuclease, wherein said second exonuclease digests the second nicked strand;
   (j) providing at least one second mutagenic oligonucleotide, wherein said at least one second mutagenic oligonucleotide anneals to the remaining mutant strand;
   (k) providing a second polymerase, wherein said second polymerase extends said at least one second mutagenic oligonucleotide around the remaining mutant strand;
   (l) providing a second ligase, wherein said second ligase ligates the extended strand to form a double stranded nucleic acid comprising a double stranded mutant nucleic acid molecule; and
   (m) purifying the double stranded mutant nucleic acid molecule from step (l).

2. The method of claim 1, wherein the nucleic acid molecule is DNA, cDNA, or genomic DNA.

3. The method of claim 1, wherein the BbvCI restriction site is at least 7 base pairs.

4. The method of any one of claim 1 or 2-3, wherein the first or second nickase is Nt.BbvCI or Nb.BbvCI.

5. The method of any one of claim 1 or 2-3, wherein the first or second exonuclease is Exonuclease I, Exonuclease III, or both.

6. The method of any one of claims 1-2 or 3-5, wherein the first or second polymerase is Q5 DNA Polymerase.

7. The method of any one of claims 1-2 or 3-6, wherein the first or second ligase is Taq DNA ligase.

8. The method of any one of claims 1-2 or 3-6, wherein the at least one first or second mutagenic oligonucleotide is provided at a primer:template ratio of between 1:5 to 1:50, wherein the at least one first or second mutagenic oligonucleotide is the template.

9. The method of claim 8, wherein the primer to template ratio is 1:5, 1:10, 1:15, 1:20, 1:25, 1:30, 1:35, 1:40, 1:45, or 1:50.

10. The method of any one of claims 1-2 or 3-9, further comprising the step of providing an enzyme to remove methylated nucleic acid molecules, hemimethylated nucleic acid molecules, or both.

11. The method of any one of claims 1-2 or 3-10, wherein the mutation efficiency is enhanced to about 50%, about 55%, about 60%, about 65%, about 70%, about 75%, about 80%, about 85%, about 90%, about 92%, or about 94%, about 95%, about 96%, about 97%, about 98%, or about 99%, wherein the enhanced mutation efficiency is characterized with increased transformants or transformation output.

12. A method of generating a double stranded mutant nucleic acid molecule comprising the steps of:
   (a) providing a double stranded wild-type nucleic acid molecule, wherein the double stranded wild-type nucleic acid molecule comprises a BbvCI nickase recognition site;
   (b) nicking one strand of the nucleic acid molecule with a first nickase to create a first nicked strand and a remaining wild-type strand;
   (c) digesting said first nicked strand with a first exonuclease;
   (d) annealing at least one first mutagenic oligonucleotide to the remaining wild-type strand;
   (e) extending said at least one first mutagenic oligonucleotide around the remaining wild-type strand with a first polymerase;
   (f) ligating the extended strand with a first ligase to form a double stranded nucleic acid comprising a mutant strand and a wild-type;
   (g) purifying the double stranded nucleic acid from step (f);
   (h) nicking the wild-type strand with a second nickase to create a second nicked strand and a remaining mutant strand;
   (i) digesting said second nicked strand with a second exonuclease;
   (j) annealing at least one second mutagenic oligonucleotide to the remaining mutant strand;
   (k) extending said at least one second mutagenic oligonucleotide around the remaining mutant strand with a second polymerase;
   (l) ligating the extended strand with a second ligase to form a double stranded mutant nucleic acid molecule; and
   (m) purifying the double stranded mutant nucleic acid molecule from step (l).

13. The method of claim 12, wherein the double stranded wild-type nucleic acid molecule is DNA, cDNA, or genomic DNA.

14. The method of claim 12, wherein the BbvCI restriction site is at least 7 base pairs.

15. The method of any one of claims 12-13 or 14, wherein the first or second nickase is Nt.BbvCI or Nb.BbvCI.

16. The method of any one of claims 12-13 or 14-15, wherein the first or second exonuclease is Exonuclease I, Exonuclease III, or both.

17. The method of any one of claims 12-13 or 14-16, wherein the first or second polymerase is Q5 DNA Polymerase.

18. The method of any one of claims 12-13 or 14-17, wherein the first or second ligase is Taq DNA ligase.

19. The method of any one of claims 12-13 or 14-18, wherein the at least one first or second mutagenic oligonucleotide is provided at a primer:template ratio of between 1:5 to 1:50, wherein the at least one first or second mutagenic oligonucleotide is the template.

20. The method of claim 19, wherein the primer to template ratio is 1:5, 1:10, 1:15, 1:20, 1:25, 1:30, 1:35, 1:40, 1:45, or 1:50.

21. The method of any one of claims 12-13 or 14-20, further comprising the step of providing an enzyme to remove methylated nucleic acid molecules, hemimethylated nucleic acid molecules, or both.

22. The method of any one of claims 12-13 or 14-21, wherein the mutation efficiency is enhanced to about 50%, about 55%, about 60%, about 65%, about 70%, about 75%, about 80%, about 85%, about 90%, about 92%, or about 94%, about 95%, about 96%, about 97%, about 98%, or about 99%, wherein the enhanced mutation efficiency is characterized with increased transformants or transformation output.

23. The method of any one of claims 12-22 for generating single-site saturation mutagenesis.

24. The method of any one of claims 12-22 for generating multi-site saturation mutagenesis.

25. The method of any one of claims 23-24, wherein the mutagenesis is a three single or one triple-mutation.

* * * * *

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcggccccac gggtcctcag cgcgcatgat                                          30

<210> SEQ ID NO 3
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gacgagctaa tatcgccatg tctcatatgt ataaaaactt cttaaagtta aacaaaatta        60
tttctagaaa g                                                             71

<210> SEQ ID NO 4
<211> LENGTH: 39
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 4
gcaaagcatt gaacaccatg accgaaagta gtgacaagt        39

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gcaaagcatt gaacaccata accgaaagta gtgacaagt        39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
acttgtcact actttcggtt atggtgttca atgctttgc        39

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ggtgattcat tctgctaa        18

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gttcagagtt ctacagtccg acgatcgcaa atgtttgggg tgtg        44

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gttcagagtt ctacagtccg acgatcctgc gatgacggta at        42

<210> SEQ ID NO 10
<211> LENGTH: 40
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 10
ccttggcacc cgagaattcc actctccaaa tttccggata                          40

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccttggcacc cgagaattcc attcgccgca ttcacccaga gt                       42

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatgatacgg cgaccaccga gatctacacg ttcagagttc tacagtccga              50

<210> SEQ ID NO 13
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caagcagaag acggcatacg agatccggtg gtgactggag ttccttggca cccgagaatt    60
c                                                                   61

<210> SEQ ID NO 14
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caagcagaag acggcatacg agatatcgtg gtgactggag ttccttggca cccgagaatt    60
cc                                                                  62
```